United States Patent
Chen et al.

(10) Patent No.: US 9,320,835 B2
(45) Date of Patent: Apr. 26, 2016

(54) POLYMER COMPOSITION ON SUBSTRATE AND SURFACE MODIFICATION METHOD

(71) Applicant: National Taiwan University, Taipei (TW)

(72) Inventors: Hsien-Yeh Chen, Taipei (TW); Sheng-Tung Huang, Taipei (TW); Meng-Yu Tsai, Taipei (TW)

(73) Assignee: National Taiwan University, Taipei (KR)

( * ) Notice: Subject to any disclaimer, the term of this patent is extended or adjusted under 35 U.S.C. 154(b) by 173 days.

(21) Appl. No.: 13/831,829

(22) Filed: Mar. 15, 2013

(65) Prior Publication Data

US 2014/0199470 A1     Jul. 17, 2014

(30) Foreign Application Priority Data

Jan. 14, 2013  (TW) ................. 102101354 A
Jan. 22, 2013  (TW) ................. 102102390 A

(51) Int. Cl.
*B32B 9/04*     (2006.01)
*A61L 31/10*    (2006.01)
*C23C 16/505*   (2006.01)
*B05D 1/00*     (2006.01)

(52) U.S. Cl.
CPC .............. *A61L 31/10* (2013.01); *C23C 16/505* (2013.01); *A61L 2400/18* (2013.01); *B05D 1/60* (2013.01)

(58) Field of Classification Search
None
See application file for complete search history.

(56) References Cited

U.S. PATENT DOCUMENTS

| 6,884,628 | B2 | 4/2005 | Hubbell et al. |
| 7,909,928 | B2 | 3/2011 | Lahann et al. |
| 8,212,225 | B2 | 7/2012 | Hutchison et al. |
| 2002/0076562 | A1 | 6/2002 | Desu et al. |
| 2008/0293164 | A1* | 11/2008 | Gaylord et al. ............. 436/536 |
| 2011/0143993 | A1* | 6/2011 | Langer et al. ............... 514/1.4 |
| 2011/0210094 | A1 | 9/2011 | Gray et al. |
| 2011/0238109 | A1 | 9/2011 | Ladet |

FOREIGN PATENT DOCUMENTS

| TW | 200900435 | 1/2009 |
| TW | 201137341 | 11/2011 |

OTHER PUBLICATIONS

Meng-Yu Tsai et al., "Vapor-based synthesis of maleimide-functionalized coating for biointerface engineering", Chem. Commun., Sep. 2012, 48, pp. 10969-10971.

* cited by examiner

*Primary Examiner* — Coris Fung
(74) *Attorney, Agent, or Firm* — Jianq Chyun IP Office

(57) ABSTRACT

Provided are a polymer composition on a substrate and a surface modification method which is non-selective to substrate materials. Chemical vapor deposition polymerization is used to deposit a maleimide-functionalized poly-p-xylylene coating on a substrate. The substrate is readily available to perform a thiol-maleimide coupling reaction under mild conditions so as to modify the surface thereof. Furthermore, through a tailored thiol-terminal molecule, a designer surface can be created via thiol-maleimide coupling on a substrate, and the resulting surface can exhibit various desired biological functions for biotechnological applications. Therefore, this modification technique can be applied to biological fields extensively.

18 Claims, 5 Drawing Sheets
(2 of 5 Drawing Sheet(s) Filed in Color)

POLYMER COMPOSITION ON SUBSTRATE AND SURFACE MODIFICATION METHOD

CROSS-REFERENCE TO RELATED APPLICATION

This application claims the priority benefit of Taiwan application serial no. 102101354, filed Jan. 14, 2013 and Taiwan application serial no. 102102390, filed Jan. 22, 2013. The entirety of each of the above-mentioned patent applications is hereby incorporated by reference herein and made a part of this specification.

BACKGROUND OF THE INVENTION

1. Field of the Invention

The invention relates to a polymer composition, and more particularly, to a polymer composition that can be formed on various substrates to modify the surfaces thereof.

2. Description of Related Art

Modern trends in biotechnology fields, such as biomaterials, biosensors, biochips, microfluidics, drug delivery, tissue engineering, cellular biology, and regenerative medicine, have targeted controlled designs to mimic and to respond to the biological environments on a molecular scale. The key factor that determines the long term performance and efficiency of biomaterials is in the surface modification of bio-substrates.

A thiol group or a thiol-containing molecule is indispensable in the maintenance of the functioning of the organism. In the applications of biotechnology, the thiol-maleimide coupling reaction is already well known. Currently, maleimide groups have been modified on the bio-substrate surface via self-assembled monolayer, linkers, polymer grafting, or silanation. However, these modification approaches still require a high-temperature environment, UV irradiation, metal catalysts, toxic solvents etc., and also require suitable modification techniques based on different substrates and different application conditions. As a result, a large knowledge base is often required in order to perform the surface modification on substrates. Therefore, an improved surface modification method applicable to the biological field is desired.

SUMMARY OF THE INVENTION

The invention provides a polymer composition that can be applied to various biological substrates to modify the surfaces thereof.

The invention also provides a surface modification method that can be conducted under mild conditions and applied to the biological field.

The invention provides a polymer composition on a substrate, which includes a maleimide-functionalized poly-p-xylylene deposited on the surface of the substrate, wherein the maleimide group of the poly-p-xylylene is bonded to the first functional group of a target molecule through a coupling reaction.

In an embodiment of the invention, the target molecule includes a biomolecule.

In an embodiment of the invention, the material of the substrate includes silicon, glass, a metal, or a polymer.

In an embodiment of the invention, the substrate includes a biological vessel, a heart stent, or a pacemaker.

In an embodiment of the invention, the first functional group includes a thiol group, and the target molecule includes a biomolecule.

In an embodiment of the invention, the coupling reaction includes a thiol-ene coupling reaction.

In an embodiment of the invention, the maleimide group includes a mono-maleimide group or a bismaleimide group, and the maleimide group is substituted or unsubstituted.

In an embodiment of the invention, the maleimide-functionalized poly-p-xylylene is represented by Formula (1) or Formula (2) below:

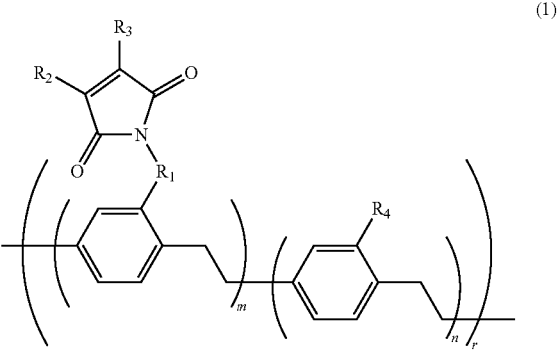

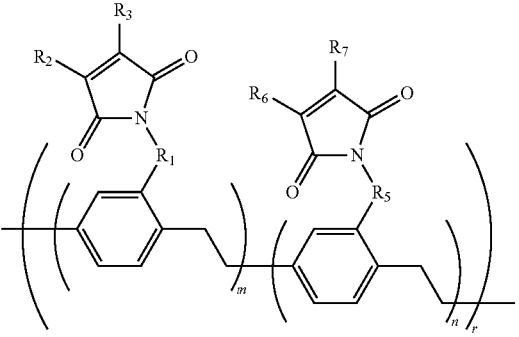

wherein, $R_1$ and $R_5$ each independently represent —$CH_2$—, —$CH_2$—$CH_2$—OC(=O)—, —$CH_2$—$CH_2$—NH—C(=O)—, —C(=O)—, or —O—$CH_2$—;

$R_2$, $R_3$, $R_4$, $R_6$, and $R_7$ each independently represent a hydrogen atom, methyl (Me), or a chlorine atom;

m and n are each independently an integer of 1 to 150; and r is an integer of 1 to 5,000.

In an embodiment of the invention, the maleimide-functionalized poly-p-xylylene is deposited by chemical vapor deposition.

The invention also provides a surface modification method including the following steps. A maleimide-functionalized paracyclophane is deposited and polymerized on a surface of a substrate by a chemical vapor deposition method, so as to form a maleimide-functionalized poly-p-xylylene on the surface of the substrate. The maleimide group of the poly-p-xylylene reacts with the first functional group of a target molecule through a coupling reaction.

In another embodiment of the invention, the target molecule includes a biomolecule.

In another embodiment of the invention, the material of the substrate includes silicon, glass, a metal, or a polymer.

In another embodiment of the invention, the substrate includes a biological vessel, a heart stent, or a pacemaker.

In another embodiment of the invention, the first functional group includes a thiol group, and the target molecule includes a biomolecule.

In another embodiment of the invention, the coupling reaction includes a thiol-ene coupling reaction.

In another embodiment of the invention, the maleimide group includes a mono-maleimide group or a bismaleimide group, and the maleimide group is substituted or unsubstituted.

In another embodiment of the invention, the maleimide-functionalized paracyclophane is represented by Formula (4) or Formula (5) below:

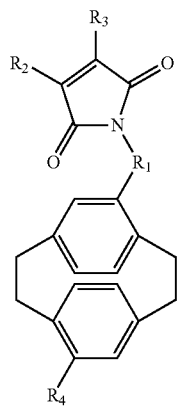

(4)

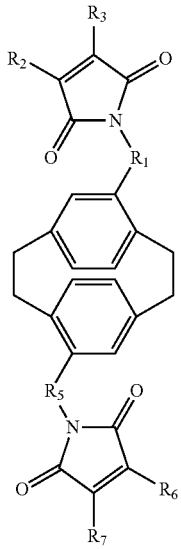

(5)

wherein, $R_1$ and $R_5$ each independently represent —$CH_2$—, —$CH_2$—$CH_2$—OC(=O)—, —$CH_2$—$CH_2$—NH—C(=O)—, —C(=O)—, or —O—$CH_2$—; and $R_2$, $R_3$, $R_4$, $R_6$, and $R_7$ each independently represent a hydrogen atom, methyl, or a chlorine atom.

In another embodiment of the invention, the maleimide-functionalized poly-p-xylylene is represented by Formula (1) or Formula (2) below:

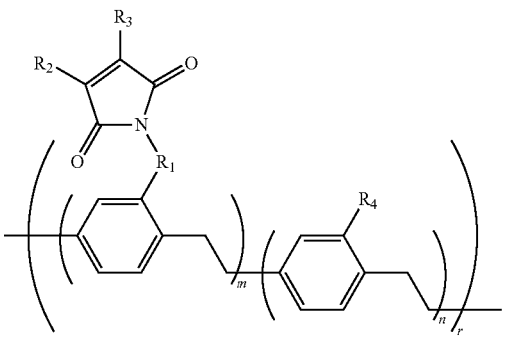

(1)

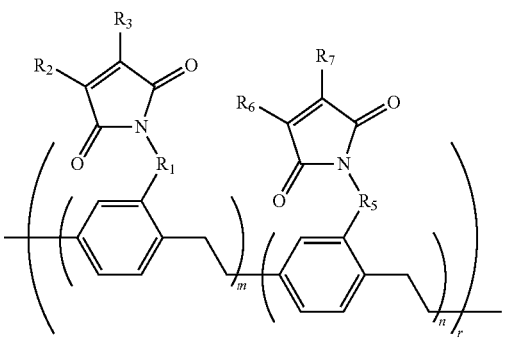

(2)

wherein, $R_1$ and $R_5$ each independently represent —$CH_2$—, —$CH_2$—$CH_2$—OC(=O)—, —$CH_2$—$CH_2$—NH—C(=O)—, —C(=O)—, or —O—$CH_2$—;

$R_2$, $R_3$, $R_4$, $R_6$, and $R_7$ each independently represent a hydrogen atom, methyl, or a chlorine atom;

m and n are each independently an integer of 1 to 150; and r is an integer of 1 to 5,000.

In another embodiment of the invention, in the chemical vapor deposition method, the pressure ranges from about 0.1 mbar to 0.3 mbar, the temperature ranges from about 550° C. to 650° C., and the deposition rate ranges from about 0.3 Å/s to 1.0 Å/s.

In another embodiment of the invention, a catalyst or a solvent is not required for the chemical vapor deposition method.

Based on the above, in the invention, a maleimide-functionalized poly-p-xylylene is, deposited and polymerized by chemical vapor deposition on a substrate such as a biological vessel, a heart stent, or a pacemaker. Accordingly, the surfaces of various substrates can be modified under mild conditions that do not require the use of a catalyst or UV irradiation.

In order to make the aforementioned features and advantages of the invention more comprehensible, embodiments are described in detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
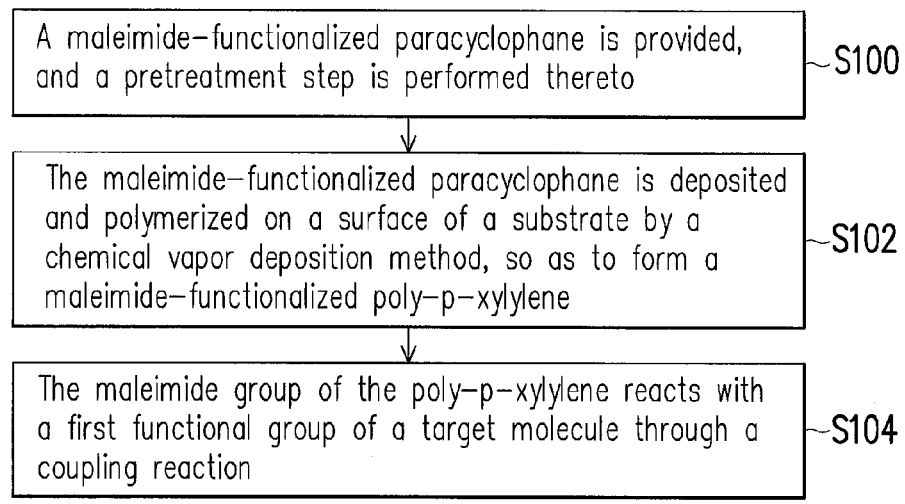
FIG. 1 illustrates a process flow chart of a surface modification method according to an embodiment of the invention.

FIG. 1 illustrates a process flow chart of a surface modification method according to an embodiment of the invention.

First, referring to step S100 of FIG. 1, a maleimide-functionalized paracyclophane is provided, and a pretreatment step is performed to the maleimide-functionalized paracyclophane.

In this embodiment, the maleimide group is, for instance, a mono-maleimide group or a bismaleimide group, and the maleimide group is substituted or unsubstituted. Moreover, the maleimide-functionalized paracyclophane is, for instance, represented by Formula (4) or Formula (5) below:

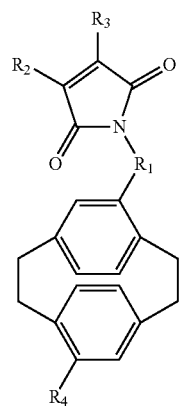

(4)

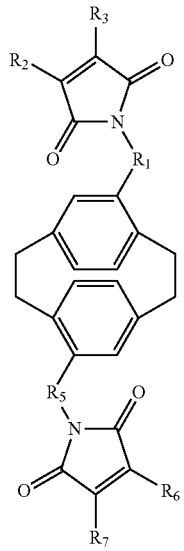

(5)

wherein $R_1$ and $R_5$ each independently represent $-CH_2-$, $-CH_2-CH_2-OC(=O)-$, $-CH_2-CH_2-NH-C(=O)-$, $-C(=O)-$, or $-O-CH_2-$; and $R_2$, $R_3$, $R_4$, $R_6$ and $R_7$ each independently represent a hydrogen atom, methyl, or a chlorine atom.

Specifically, the maleimide-functionalized paracyclophane is, for instance, represented by one of Formula (8a) to Formula (8e) below:

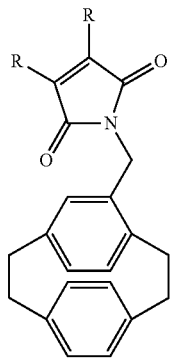

Formula (8a)

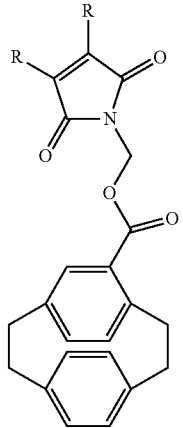

Formula (8b)

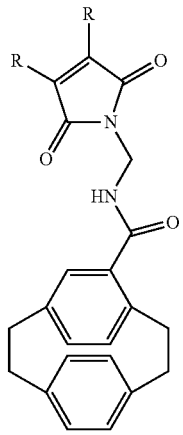

Formula (8c)

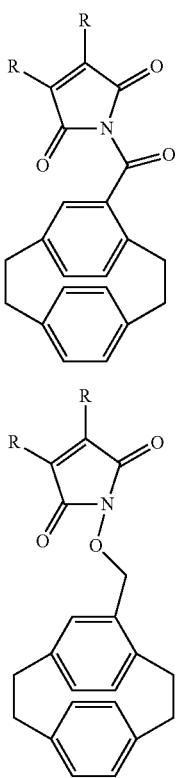

Formula (8d)

Formula (8e)

wherein R represents a hydrogen atom, methyl, or a chlorine atom.

More specifically, the maleimide-functionalized paracyclophane is, for instance, represented by Formula (6) below:

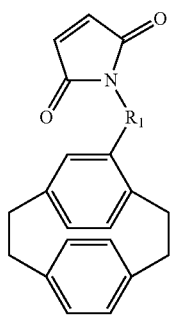

(6)

In this embodiment, in the pretreatment step, the maleimide-functionalized paracyclophane is subjected to sublimation under specific temperature and pressure conditions, and followed by pyrolysis in a pyrolysis zone. The sublimation temperature ranges, for instance, from about 90° C. to 110° C., preferably from about 100° C. to 110° C. The sublimation pressure ranges, for instance, from about 0.1 mbar to 0.5 mbar, preferably from about 0.1 mbar to 0.3 mbar. The temperature of the pyrolysis zone is, for instance, maintained between about 500° C. to 700° C., preferably between about 550° C. to 680° C.

Then, referring to step S102 of FIG. 1, the maleimide-functionalized paracyclophane is deposited and polymerized on the surface of a substrate by a chemical vapor deposition method, so as to form a maleimide-functionalized poly-p-xylylene.

In this embodiment, in the chemical vapor deposition method, the pressure ranges, for instance, from about 0.1 mbar to 0.3 mbar; the substrate temperature ranges, for instance, from about −30° C. to 40° C., preferably from about 0° C. to 30° C., and more preferably from about 5° C. to 15° C.; and the deposition rate ranges, for instance, from about 0.3 Å/s to 1.0 Å/s. Moreover, a catalyst or a solvent is not used in the chemical vapor deposition method.

In this embodiment, the material of the substrate is, for instance, silicon, glass, a metal, or a polymer. More specifically, the metal is, for instance, titanium (Ti), silver (Ag), or gold (Au). The polymer is, for instance, poly(methyl methacrylate) (PMMA) or polystyrene. Moreover, the substrate is, for instance, a biological vessel, a heart stent, or a pacemaker. Furthermore, the parylene (or poly-p-xylene) of the invention is certified by the Food and Drug Administration (FDA), and can be, for instance, a coating used in a medical equipment such as a biological vessel, a heart stent, or a pacemaker.

In this embodiment, the maleimide-functionalized poly-p-xylylene is represented by, for instance, Formula (1) or Formula (2) below:

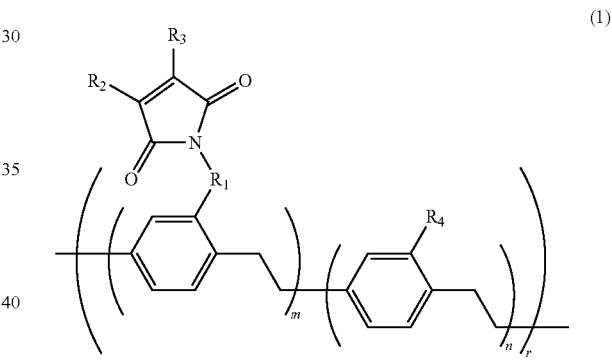

(1)

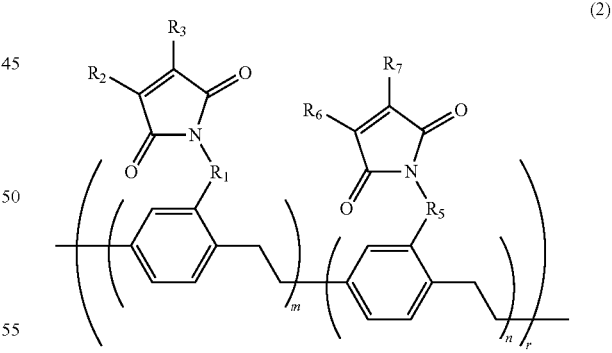

(2)

In particular, $R_1$ and $R_5$ each independently represent $-CH_2-$, $-CH_2-CH_2-OC(=O)-$, $-CH_2-CH_2-NH-C(=O)-$, $-C(=O)-$, or $-O-CH_2-$; $R_2$, $R_3$, $R_4$, $R_6$ and $R_7$ each independently represent a hydrogen atom, methyl, or a chlorine atom; m and n are each independently an integer of 1 to 150, and r is an integer of 1 to 5,000.

Specifically, the maleimide-functionalized poly-p-xylylene is, for instance, represented by one of Formula (9a) to Formula (9e) below:

(9a)
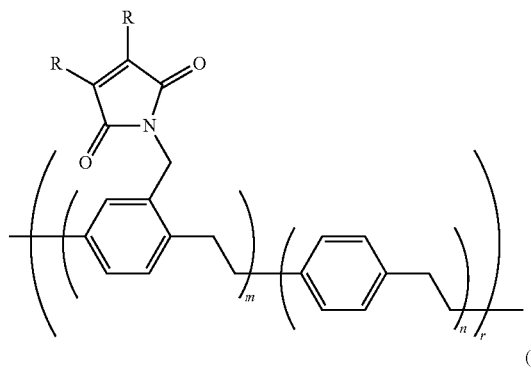

(9b)
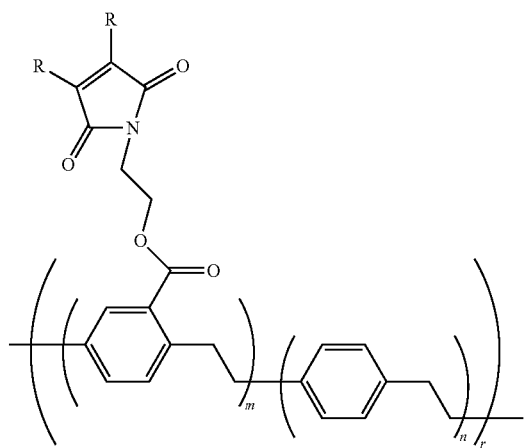

(9c)
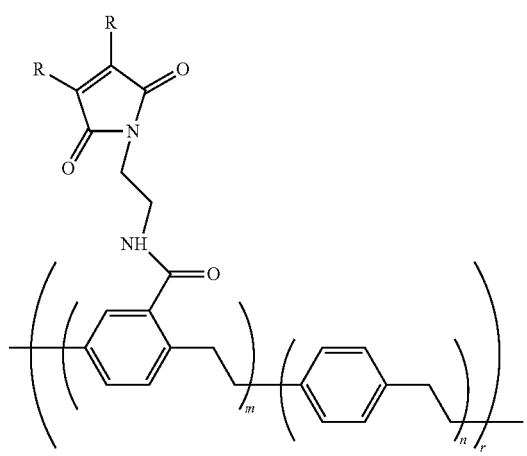

(9d)
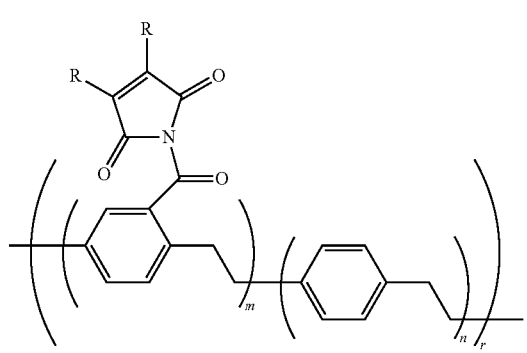

(9e)
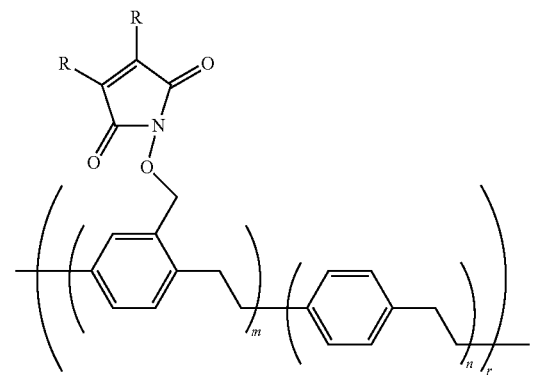

wherein R represents a hydrogen atom, methyl, or a chlorine atom, m and n are each independently an integer of 1 to 150, and r is an integer of 1 to 5,000.

More specifically, the maleimide-functionalized poly-p-xylylene is, for instance, represented by Formula (3) below:

(3)
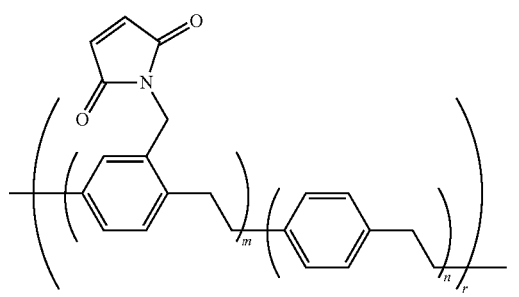

wherein m and n are each independently an integer of 1 to 150, and r is an integer of 1 to 5,000.

Then, referring to step S104 of FIG. 1, the maleimide group of the maleimide-functionalized poly-p-xylylene reacts with the first functional group of a target molecule through a coupling reaction.

In this embodiment, the target molecule is, for instance, a biomolecule, and more specifically, DNA (deoxyribonucleic acid), RNA (ribonucleic acid), protein, amino acid, growth factor, oligosaccharide, or hormone. Moreover, the first functional group is, for instance, a thiol group, which is not only important for biological systems, but can also exist in abundance. Also, the thiol group is readily modified onto biomolecules. In the case that the first functional group is a thiol group, the surface modification can be achieved by a Michael-type addition between the maleimide group and the thiol group, such as through a thiol-ene coupling reaction between the unsaturated carbon-carbon bond of the maleimide group and the thiol group.

Generally, the target molecule also has a different group in addition to the first functional group. It is noted that a regioselective coupling reaction is only carried out between the first functional group in the local region of the target molecule and the maleimide group of the maleimide-functionalized poly-p-xylylene, so as to bond the target molecule to the maleimide-functionalized poly-p-xylylene.

In another embodiment of the invention, a polymer composition on a substrate is provided, wherein the polymer composition includes a maleimide-functionalized poly-p-xylylene deposited on the surface of a substrate, and the maleimide group of the poly-p-xylylene is bonded to the first functional group of a target molecule through a coupling reaction. In this embodiment, the maleimide-functionalized poly-p-xylylene is deposited by chemical vapor deposition, for instance. Moreover, the substrate, the maleimide-functionalized poly-p-xylylene, the target molecule, and first functional group have been described above, and are therefore not repeated herein.

Accordingly, in the invention, a maleimide-functionalized poly-p-xylylene can be deposited and polymerized on various substrates with chemical vapor deposition, and the surface modification can be achieved by a coupling reaction between the maleimide group of the maleimide-functionalized poly-p-xylylene and the specific functional group of a target molecule (e.g. biomolecule). Moreover, the reaction conditions for the surface modification are simple, the reaction is fast, and the surface modification is stereoselective. Furthermore, the surface modification can even be performed at room temperature in the presence of oxygen and water, without the use of any expensive and potentially toxic catalyst.

Below, a synthesis embodiment and two experimental embodiments are used to explain the invention more specifically. However, the invention is not limited to the embodiments.

Embodiment 1

First, 4-N-maleimidomethyl-[2,2]paracyclophane 4 is synthesized. Referring to process (a) below, in a nitrogen environment, titanium (IV) chloride (TiCl$_4$) (8.4 mL, 77 mmol) is added slowly to a market-purchased solution of [2,2]paracyclophane 1 (8.0 g, 38 mmol) in anhydrous CH$_2$Cl$_2$ (400 mL). The mixture is stirred for 20 minutes, followed by the dropwise addition of α,α-dichloromethyl methyl ether (CHCl$_2$OCH$_3$) (4.0 mL, 44 mmol) at room temperature. The mixture is then continuously stirred for 6 hours to perform a Rieche formylation. Then, the mixture is poured into water (200 mL) and stirred for another 2 hours. The solution is washed with 3M HCl (2×300 mL) and then with water (2×300 mL), and dried over MgSO$_4$. After filtration and removal of the solvent, the crude product is purified using hexane/dichloromethane (5/1) as eluent to yield 4-formyl-[2,2]paracyclophane 2 as crystals (6.6 g, 83%). The crystals are dissolved in a mixture of MeOH (200 mL) and anhydrous Tetrahydrofuran (THF) (10 mL). Then, sodium borohydride (NaBH$_4$) (2.1 g, 28 mmol) is added carefully and the mixture is stirred at room temperature for 3 hours. The excess NaBH$_4$ is then decomposed by addition of water. The resulting solution is then diluted by ethyl acetate (200 mL), washed with 3M HCl (3×200 mL) and water (2×200 mL), and dried over MgSO$_4$. After filtration and removal of the solvent, 4-(hydroxymethyl)-[2,2]paracyclophane 3 is obtained as crystals (6.0 g, 75%). Next, the resulting 4-(hydroxymethyl)-[2,2]paracyclophane 3 (6.0 g) and triphenylphosphine (PPh$_3$) (13.1 g) are dissolved in anhydrous THF, to which diisopropyl azodicarboxylate (DIAD) (10 mL) is added carefully and the mixture is stirred at room temperature for 20 minutes. Then, a previously prepared maleimide solution (4.9 g maleimide in 30 mL anhydrous THF) is added to the resulting mixture and stirred at room temperature for 24 hours. The solution is then diluted with dichloromethane (200 mL), washed with 3M HCl (3×200 mL) and water (2×200 mL), and dried over MgSO$_4$. The crude product is purified using hexane/ethyl acetate (5/1) to yield 4-N-maleimidomethyl-[2,2]paracyclophane 4 as crystals (5.2 g, 65%).

Then, referring to process (b) below, poly[(4-N-maleimidomethyl-p-xylylene)-co-(p-xylylene)]5 is prepared from 4-N-maleimidomethyl-[2,2]paracyclophane 4 with a CVD polymerization process, wherein m:n=1:1. Throughout the process, a constant argon flow rate of 10 sccm and a system pressure of 75 mTorr are maintained. The sublimation temperature is set between 110° C. and 120° C., and the pyrolysis temperature is set at 580° C. Under these conditions, CVD polymerization occurs spontaneously on substrates that are placed on a rotating, cooled (15° C.) sample holder. A deposition rate of about 0.3 Å/s is monitored on the basis of in situ quartz crystal microbalancing analysis. Moreover, using an ellipsometer, the thickness of the resulting maleimide-functionalized poly-p-xylylene coating deposited is measured in the range of 60 nm to 80 nm.

(a)

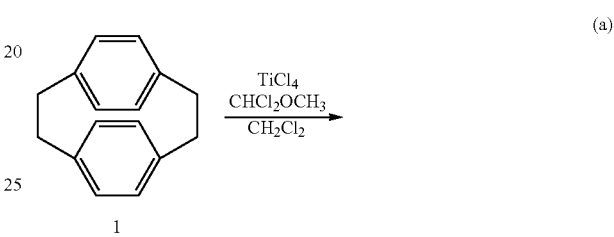

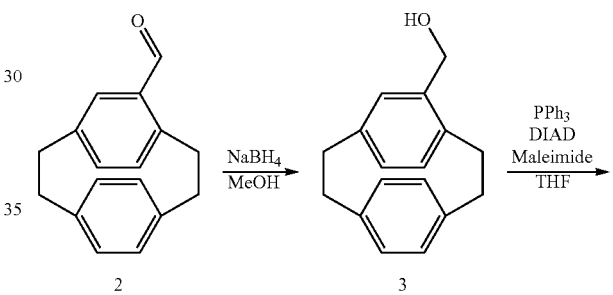

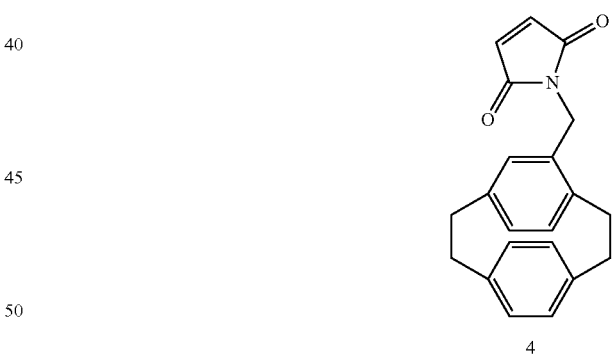

(b)

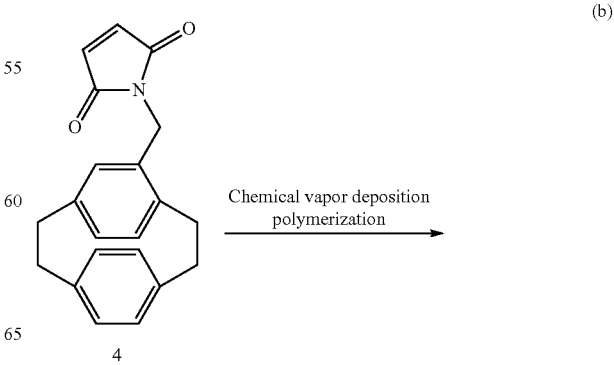

-continued

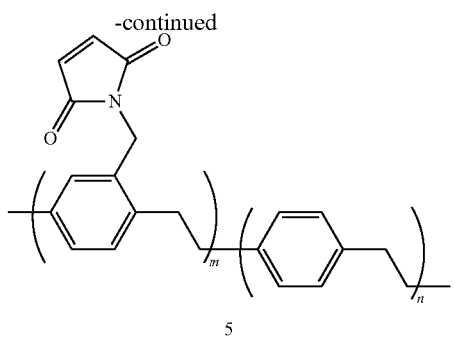

5

Embodiment 2

In order to test the feasibility and reactivity of the surface modification of the substrate having a maleimide-functionalized poly-p-xylylene coating, microcontact printing (μCP) technique is used for the experiment in order to confine the reaction locations. The concept of the technique is similar to that of the stamp in that the technique can use flexible poly (dimethyl)siloxane (PDMS) as a stamp. Moreover, coating can be performed on the PDMS stamp. The coated PDMS stamp can be in micro-pressure contact with the substrate, so as to imprint the coating (similar to ink) on the protruding features of the stamp to the substrate.

In embodiment 2, every step is performed at room temperature (25° C.) and a humidity of 55%. First, referring to FIG. 2A, a PDMS stamp 202 and a substrate 200 are prepared, wherein the substrate 200 has a maleimide-functionalized poly-p-xylylene coating. The substrate 200 is a poly(methyl methacrylate) (PMMA) substrate. For ease of observation, the protruding features 204 of the PDMS stamp 202 are formed into a plurality of L×L (50 μm×50 μm) blocks arranged in array, and the spacing D between adjacent blocks is 50 μm. Moreover, 2 minutes of surface modification is performed on the PDMS stamp 202 using 10 W of oxygen plasma, and then RF (radio frequency) wave energy is used to form the oxygen into free radicals. Due to the high activity of the oxygen free radicals, reaction between the oxygen free radicals and the surface of the PDMS stamp 202 occurs, and a negatively-charged and hydrophilic surface is thus activated and produced, which can facilitate subsequent irreversible adhesion.

Figure 2A:
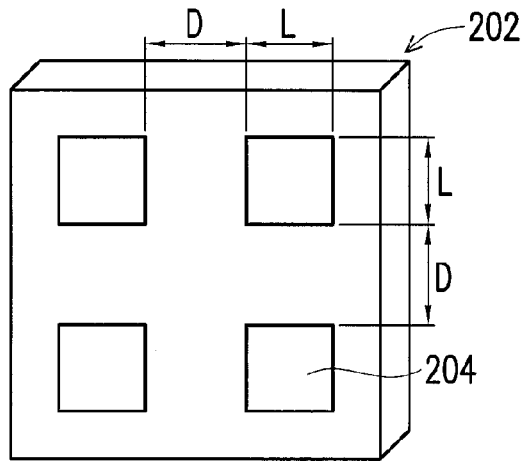
FIG. 2A to FIG. 2C are schematic diagrams each illustrating a process of a surface modification according to an embodiment of the invention.
Figure 2A:
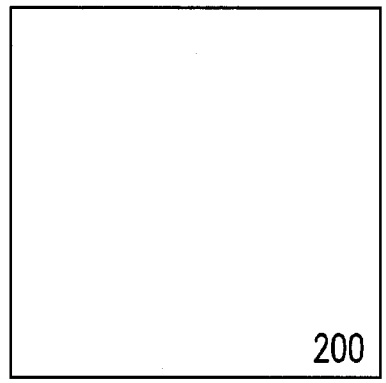
Figure 2B:
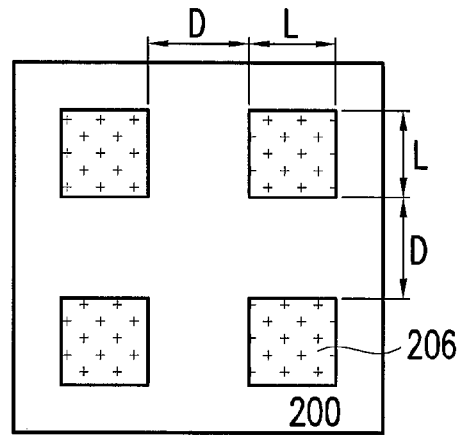

Then, referring to FIG. 2B, a 400 mg/mL thiol-polyethylene glycol (thiol-PEG) solution is prepared, wherein the solvent is deionized water. Then, the resulting solution is coated on the protruding features 204 of the PDMS stamp 202, and the PDMS stamp 202 is imprinted on the substrate 200 having maleimide-functionalized poly-p-xylylene for 2 hours. Using the thiol-ene coupling reaction between the thiol group and the maleimide group, a patterned substrate 200 having PEG-modified areas 206 is formed. The PEG moieties are well known for their anti-fouling property and are used widely to suppress nonspecific bindings of small biological molecules, proteins, bacteria or cell adhesions.

Figure 2C:
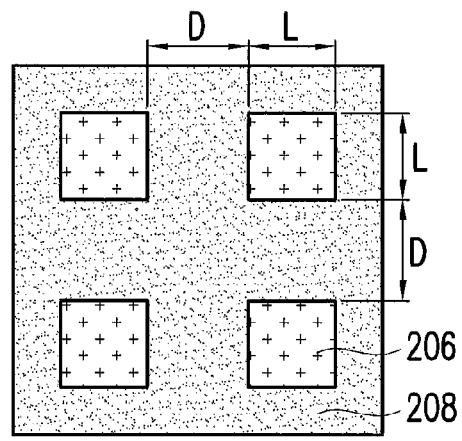

Then, referring to FIG. 2C, fluorescent dye Alexa Fluor 546 having fibrinogen bonded is used to test the anti-fouling property of the substrate 200 after the surface modification. A 100 μg/mL of protein solution is prepared, and then the patterned substrate 200 with the PEG-modified areas 206 is immersed in the protein solution for 5 minutes. Next, phosphate-buffered saline (PBS) (pH=7.4) is used to rinse off the excess protein. Then, the substrate 200 is immersed in fluorescent dye Alexa Fluor 546 having fibrinogen bonded, and a fluorescent dye layer 208 is formed on the surface of the substrate 200.

Figure 3:
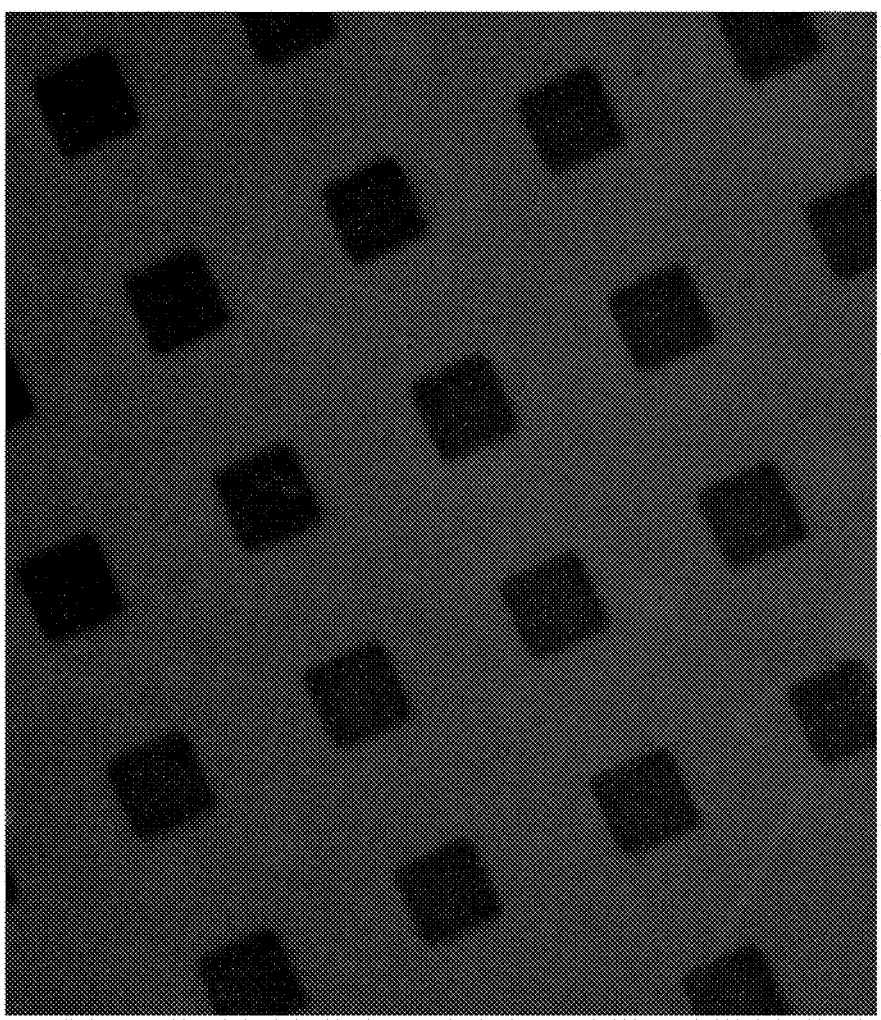
FIG. 3 is a fluorescent micrograph of a substrate surface.

As shown in FIG. 3, it is observed with a Nikon TE2000-U fluorescence microscope that the fibrinogen only selectively adheres to the unmodified PEG area. Therefore, the level of protein contamination in the PEG-modified areas is significantly less than that of the unmodified PEG area. The result shows that thiol-PEG can be reliably and effectively used to conduct the surface modification on the substrate via the bonding between the maleimide group of the substrate and the thiol group.

Embodiment 3

Figure 4A:
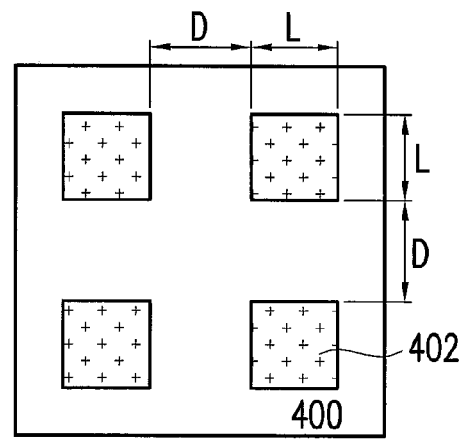
FIG. 4A to FIG. 4B are schematic diagrams each illustrating a process of a surface modification according to another embodiment of the invention.

First, referring to FIG. 4A, the method of FIG. 2A to FIG. 2B of embodiment 2 is performed, and a patterned substrate 400 having PEG-modified areas 402 is formed. The substrate 400 is a polystyrene substrate.

Figure 4B:
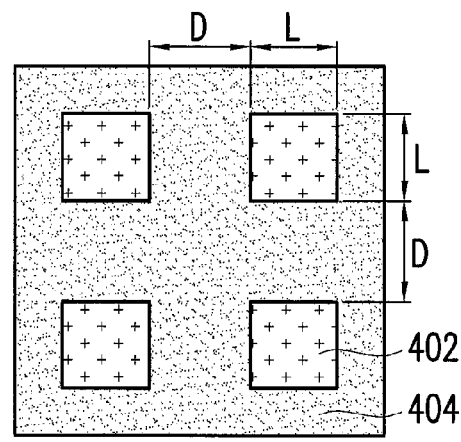

Then, referring to FIG. 4B, CREDV (cys-arg-glu-asp-val) peptide (4 mg/mL) is coated on a flat stamp that does not contain protruding features. Next, the stamp is imprinted on the selectively PEG-modified substrate 400 for 2 hours, and unreacted CREDV peptide is removed with deionized water. As a result, a bonding occurs between the maleimide group (which is not bonded to a thiol group) on the substrate 400 and the CREDV peptide, and a CREDV peptide layer 404 is formed on the surface of the substrate 400.

Here, since the CREDV peptide can be used to selectively bond to various endothelial cells, bovine aorta endothelial cells (BAEC) are used to incubate an in vitro culture on the surface-modified substrate, and the result of the cell culture is observed over time.

Figure 5:
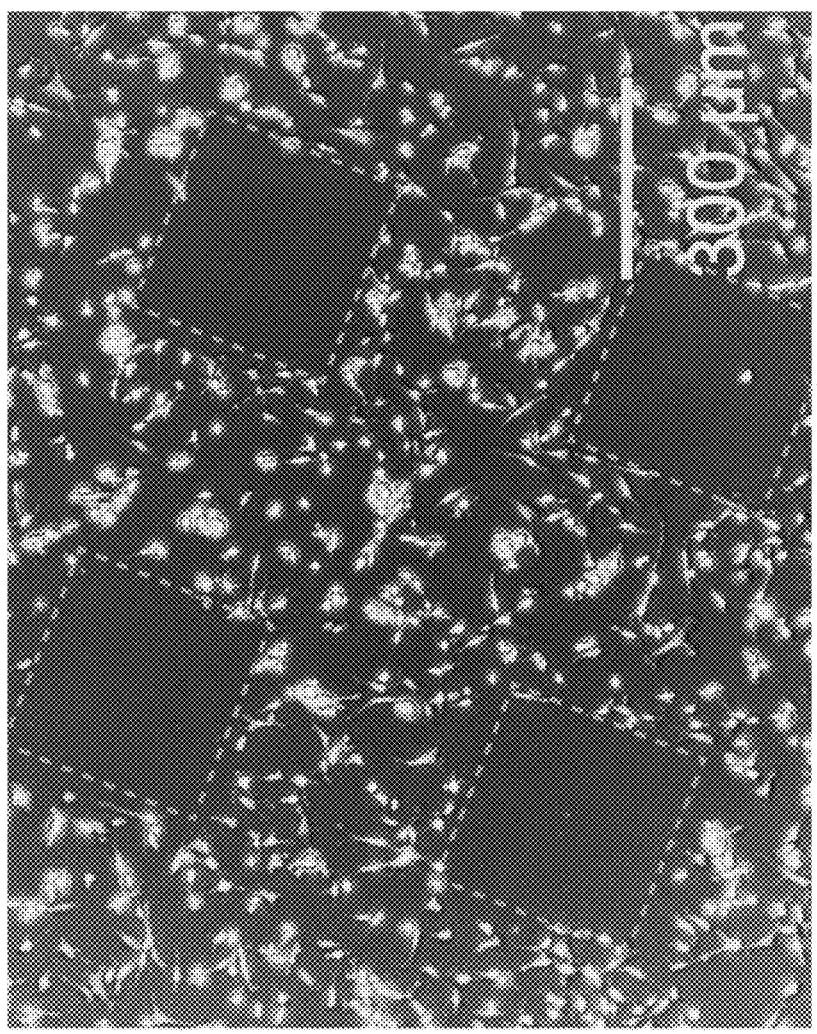
FIG. 5 is a phase contrast micrograph of a substrate surface.

As shown in FIG. 5, it is observed with a Nikon TE2000-U phase contrast microscope that, after the cells are incubated for 10 hours, the CREDV peptide-modified area on the substrate is confluent with endothelial cells. However, cell adsorption and cell growth are not observed in the PEG-modified areas. Moreover, the longer the cell incubation is, the denser the cell culture becomes. As a result, the contrast between the CREDV peptide-modified area and each PEG-modified area on the substrate becomes more apparent. The result shows that thiol-PEG can be reliably and effectively used to conduct the surface modification on the substrate via the bonding between the maleimide group of the substrate and the thiol group.

Based on the above, the invention provides a maleimide-functionalized poly-p-xylylene coating that can be prepared by a chemical vapor deposition method. Due to the features of chemical vapor deposition, a nanoscale coating without pinholes can be prepared, and the coating can be evenly deposited on various materials. More importantly, solvents, catalysts, and initiators are not needed.

Moreover, since the functional polymer coating has a maleimide group, other important biomolecules can be immobilized thereto through a bonding manner, and thus, the surface modification can be achieved. Furthermore, the surface modification has rapidity and specificity even under the conditions of room temperature and atmospheric pressure, in presence of oxygen and water, and without the use of catalysts.

The surface modification method of the invention can be applied to biological fields, such as surface antifouling, protein exclusion, and the control of cell adsorption, and more particularly, DNA-peptide coupling, fluorescent dye labeling, surface immobilization of molecules etc. Moreover, the polymer composition on the substrate and the surface modification method provided by the invention are not complex, and therefore can be readily integrated in current biological materials or medical equipment.

Although the invention has been described with reference to the above embodiments, it will be apparent to one of the ordinary skill in the art that modifications and variations to the described embodiments may be made without departing from the spirit and scope of the invention. Accordingly, the scope of the invention will be defined by the attached claims not by the above detailed descriptions.

What is claimed is:

1. A polymer composition on a substrate, comprising:
a maleimide-functionalized poly-p-xylylene, deposited on a surface of the substrate, wherein a maleimide group of the maleimide-functionalized poly-p-xylylene is bonded to a first functional group of a target molecule through a coupling reaction,
wherein the maleimide-functionalized poly-p-xylylene is represented by Formula (1) or Formula (2) below:

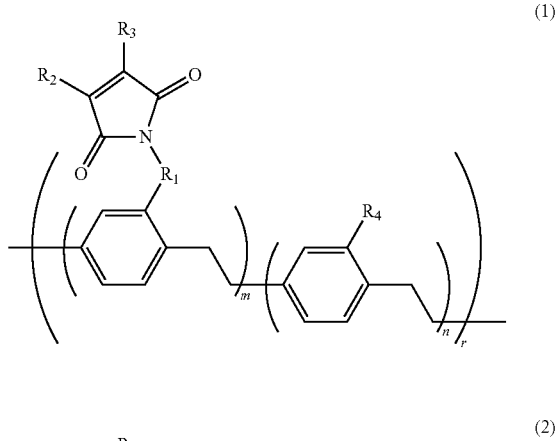

(1)

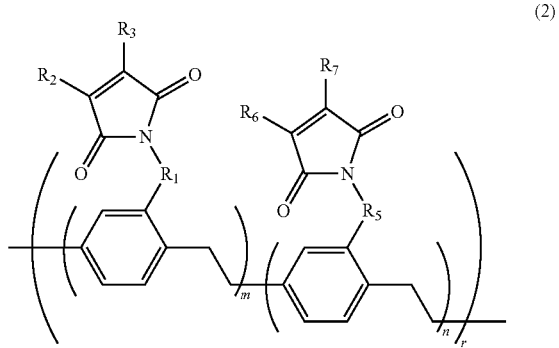

(2)

wherein,
$R_1$ and $R_5$ each independently represent —$CH_2$—, —$CH_2$—$CH_2$—$OC(=O)$—, —$CH_2$—$CH_2$—$NH$—$C(=O)$—, —$C(=O)$—, or —$O$—$CH_2$—;
$R_2$, $R_3$, $R_4$, $R_6$, and $R_7$ each independently represent a hydrogen atom, methyl, or a chlorine atom;
m and n are each independently an integer of 1 to 150; and
r is an integer of 1 to 5,000.

2. The polymer composition of claim 1, wherein the target molecule comprises a biomolecule.

3. The polymer composition of claim 1, wherein a material of the substrate comprises silicon, glass, a metal, or a polymer.

4. The polymer composition of claim 1, wherein the substrate comprises a biological vessel, a heart stent, or a pacemaker.

5. The polymer composition of claim 1, wherein the first functional group comprises a thiol group, and the target molecule comprises a biomolecule.

6. The polymer composition of claim 1, wherein the coupling reaction comprises a thiol-ene coupling reaction.

7. The polymer composition of claim 1, wherein the maleimide group comprises a mono-maleimide group or a bismaleimide group, and the maleimide group is substituted or unsubstituted.

8. The polymer composition of claim 1, wherein the maleimide-functionalized poly-p-xylylene is deposited by chemical vapor deposition.

9. A surface modification method, comprising:
depositing and polymerizing a maleimide-functionalized paracyclophane on a surface of a substrate by a chemical vapor deposition method, so as to form a maleimide-functionalized poly-p-xylylene on the surface of the substrate; and
reacting a maleimide group of the maleimide-functionalized poly-p-xylylene with a first functional group of a target molecule through a coupling reaction,
wherein the maleimide-functionalized poly-p-xylylene is represented by Formula (1) or Formula (2) below:

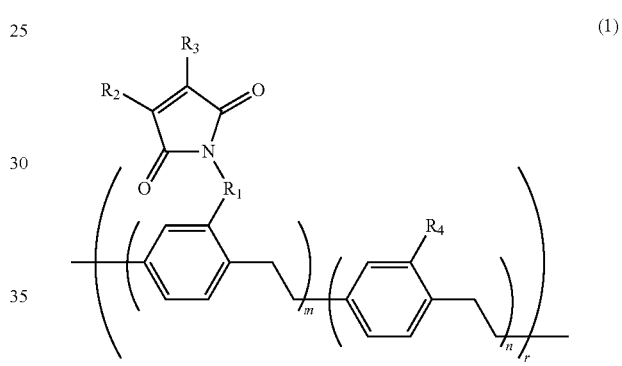

(1)

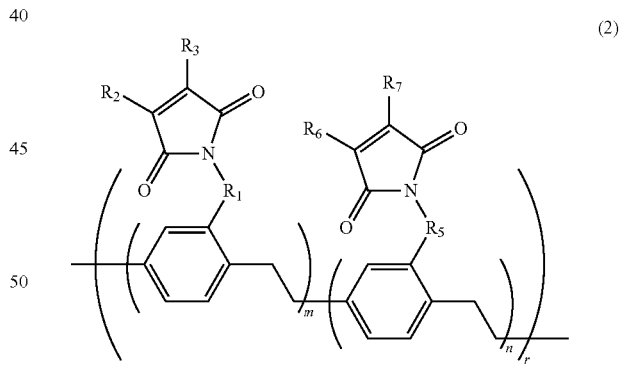

(2)

wherein,
$R_1$ and $R_5$ each independently represent —$CH_2$—, —$CH_2$—$CH_2$—$OC(=O)$—, —$CH_2$—$CH_2$—$NH$—$C(=O)$—, —$C(=O)$—, or —$O$—$CH_2$—;
$R_2$, $R_3$, $R_4$, $R_6$, and $R_7$ each independently represent a hydrogen atom, methyl, or a chlorine atom;
m and n are each independently an integer of 1 to 150; and
r is an integer of 1 to 5,000.

10. The surface modification method of claim 9, wherein the target molecule comprises a biomolecule.

11. The surface modification method of claim 9, wherein a material of the substrate comprises silicon, glass, a metal, or a polymer.

12. The surface modification method of claim 9, wherein the substrate comprises a biological vessel, a heart stent, or a pacemaker.

13. The surface modification method of claim 9, wherein the first functional group comprises a thiol group, and the target molecule comprises a biomolecule.

14. The surface modification method of claim 9, wherein the coupling reaction comprises a thiol-ene coupling reaction.

15. The surface modification method of claim 9, wherein the maleimide group comprises a mono-maleimide group or a bismaleimide group, and the maleimide group is substituted or unsubstituted.

16. The surface modification method of claim 9, wherein the maleimide-functionalized paracyclophane is represented by Formula (4) or Formula (5) below:

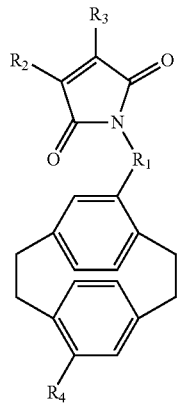

(4)

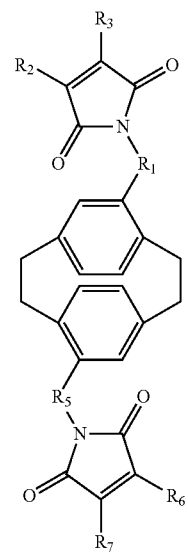

(5)

wherein,
$R_1$ and $R_5$ each independently represent —$CH_2$—, —$CH_2$—$CH_2$—$OC(=O)$—, —$CH_2$—$CH_2$—$NH$—$C(=O)$—, —$C(=O)$—, or —$O$—$CH_2$—; and
$R_2$, $R_3$, $R_4$, $R_6$, and $R_7$ each independently represent a hydrogen atom, methyl, or a chlorine atom.

17. The surface modification method of claim 9, wherein in the chemical vapor deposition method, a pressure ranges from 0.1 mbar to 0.3 mbar, a temperature ranges from 550° C. to 650° C., and a deposition rate ranges from 0.3 Å/s to 1.0 Å/s.

18. The surface modification method of claim 9, wherein a catalyst or a solvent is not required for the chemical vapor deposition method.

\* \* \* \* \*

UNITED STATES PATENT AND TRADEMARK OFFICE
CERTIFICATE OF CORRECTION

PATENT NO. : 9,320,835 B2
APPLICATION NO. : 13/831829
DATED : April 26, 2016
INVENTOR(S) : Hsien-Yeh Chen, Sheng-Tung Huang and Meng-Yu Tsai Page 1 of 1

It is certified that error appears in the above-identified patent and that said Letters Patent is hereby corrected as shown below:

To correct the following item on the Title page of the Letters Patent:

(73) Assignee: NATIONAL TAIWAN UNIVERSITY, Taipei (TW)

Signed and Sealed this
Twenty-sixth Day of July, 2016

Michelle K. Lee
*Director of the United States Patent and Trademark Office*